US012746130B2

(12) United States Patent
Dusterhoft et al.

(10) Patent No.: US 12,746,130 B2
(45) Date of Patent: Sep. 29, 2026

(54) AUTO-LOCKING EXPANDABLE CORPECTOMY COLUMN

(71) Applicant: Astura Medical Inc., Irving, TX (US)

(72) Inventors: Ross Dusterhoft, Irving, TX (US); Thomas Purcell, Irving, TX (US)

(73) Assignee: ASTURA MEDICAL, INC, Irving, TX (US)

( * ) Notice: Subject to any disclaimer, the term of this patent is extended or adjusted under 35 U.S.C. 154(b) by 0 days.

(21) Appl. No.: 18/920,851

(22) Filed: Oct. 19, 2024

(65) Prior Publication Data

US 2026/0108360 A1 Apr. 23, 2026

Related U.S. Application Data

(60) Provisional application No. 63/544,784, filed on Oct. 18, 2023.

(51) Int. Cl.

*A61F 2/44* (2006.01)
*A61F 2/30* (2006.01)

(52) U.S. Cl.

CPC .... *A61F 2/446* (2013.01); *A61F 2002/30092* (2013.01); *A61F 2002/30405* (2013.01); *A61F 2002/30523* (2013.01); *A61F 2002/3055* (2013.01); *A61F 2002/30553* (2013.01); *A61F 2002/30565* (2013.01); *A61F 2002/30579* (2013.01)

(58) Field of Classification Search

CPC ................ A61F 2/442; A61F 2002/443; A61F 2002/446; A61F 2002/4465
USPC ........................................... 623/17.11–17.16
See application file for complete search history.

(56) References Cited

U.S. PATENT DOCUMENTS 8,591,587 B2 * 11/2013 Refai .................... A61F 2/4637 623/17.15
2004/0088054 A1 5/2004 Berry
2014/0107787 A1 * 4/2014 Stinchfield ................ A61F 2/44 623/17.16
2014/0156006 A1 * 6/2014 Bannigan .................. A61F 2/44 623/17.15
2022/0125596 A1 4/2022 Valkoun et al.
2022/0183854 A1 6/2022 Altarac et al.

OTHER PUBLICATIONS

International Search Report and Written Opinion in PCT Application No. PCT/US2024/052146 dated Jan. 17, 2025.

* cited by examiner

*Primary Examiner* — Eduardo C Robert
*Assistant Examiner* — Christina Negrelli Rodriguez
(74) *Attorney, Agent, or Firm* — Michael R Shevlin

(57) ABSTRACT

A vertebral body replacement system that includes an auto-locking system that is easy to use without additional instrumentation.

21 Claims, 7 Drawing Sheets

AUTO-LOCKING EXPANDABLE CORPECTOMY COLUMN

CROSS-REFERENCE TO RELATED APPLICATIONS

This application claims the benefit of U.S. Provisional Application No. 63/544,784, titled AUTO-LOCKING EXPANDABLE CORPECTOMY COLUMN, filed Oct. 18, 2023, which is incorporated herein by reference.

This application related to U.S. Provisional Application No. 63/544,783, titled EXPANDABLE CORPECTOMY MODULAR ENDPLATE CONNECTION, filed Oct. 18, 2023, which is incorporated herein by reference.

FIELD

The present invention relates generally to the field of surgery, and more specifically, to a vertebral body replacement device (i.e., "VBR") for placement in spinal fusion surgery.

BACKGROUND

A corpectomy or vertebrectomy is a surgical procedure that involves removing all or part of the vertebral body, usually as a way to decompress the spinal cord and nerves. When the vertebral body has been removed, the surgeon performs a vertebral fusion. Because a space in the column remains from the surgery, the surgeon may insert a vertebral body replacement system to fill the space.

Current vertebral body replacement systems typically consist of an expanding column-like central member with two endplates on either end. Current systems also typically require an additional component to fixate the height of central column after expansion. This component is typically a setscrew that is inserted and torqued to the expanded column after the inserter is detached. This requires additional time during surgery and additional instrumentation in the set.

Some prior art solutions include an automatic locking mechanism consisting of a flexible tab member that is engaged and disengaged by the inserter. The tab member is located within one of many cutouts of the threaded gear component. The primary disadvantage of this automatic locking feature is the requirement to be operated by instrumentation. If the column needs to be adjusted in height, an inserter or equivalent instrument must be re-engaged with the implant which may be difficult during surgery. An additional disadvantage of this mechanism is the lack of any tactile, visual, or audible feedback that the implant is locked.

It would be desirable to develop an auto-locking system that is easy to use without additional instrumentation.

SUMMARY

Disclosed is a vertebral body replacement system that includes an auto-locking system that is easy to use without additional instrumentation.

DETAILED DESCRIPTION

The vertebral body replacement system disclosed includes an auto-locking system that is easy to use without additional instrumentation.

Some of the features of the disclosed vertebral body replacement system include:

- The springs that are configured automatically locate into the locked position under their own power (without any outside influence such as an inserter).
- The springs provide tactile and audible feedback that the implant is locked.
- The springs provide tactile and audible feedback that the implant is expanding or collapsing.
- The springs lock the height of the column without any additional components or instruments.
- The springs do not have any toggle in the locked position as they are still compressed onto the drive gear's track.

The improvements made by the vertebral body replacement system disclosed include:

- Inventory is reduced through the absence of set screws or instrumentation needed to operate the expandable column.
- Expansion and locking of the expandable column are communicated to the user through audible and tactile feedback.
- Toggle within the implant is reduced through the springs' interaction with the drive gear.
- The springs will always locate into the locked position allowing the column to "re-lock" even if some collapse is experienced.
- The auto-locking mechanism is low-profile allowing for large graft windows and other mechanisms within the implant.

The invention in this disclosure is non-obvious for the below reasons:

- The use of nitinol to generate friction to prevent the collapse of an expanded implantable column.
- The absence of additional components or instrumentation to lock an expandable column.
- An automatic locking mechanism that provides tactile and audible communication to the user is novel.

Figure 1:
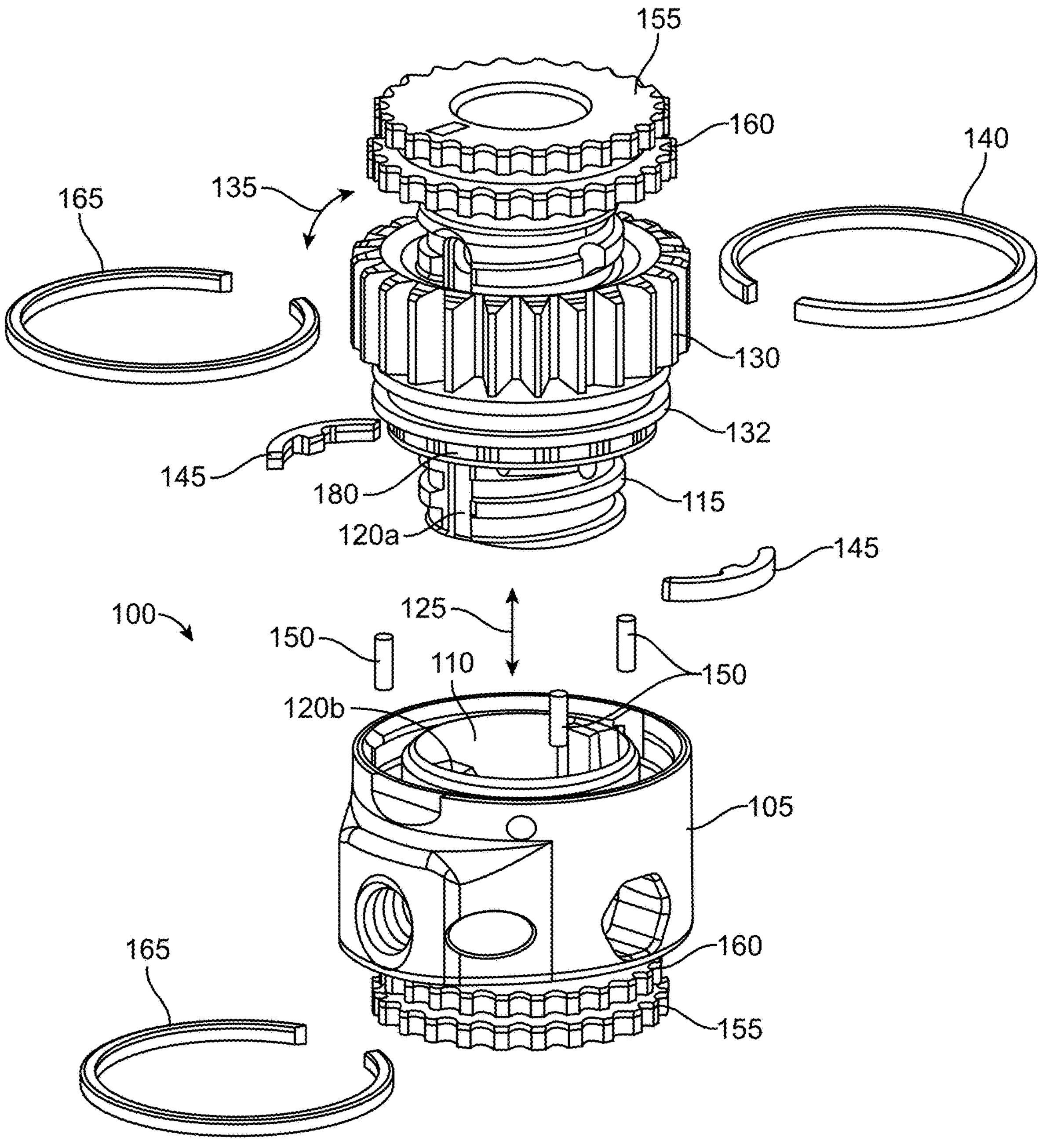
FIG. 1 is an exploded perspective view showing one embodiment of an expandable column.

FIG. 1 is an exploded perspective view showing one embodiment of an expandable column 100 having a body 105 with a central opening 110, and a threaded column 115 is configured to sliding fit within the central opening 110. The threaded column 115 may be axially translated 125 with a drive gear 130 that is threaded onto the threaded column 115. The drive gear 125 includes internal threads rotatingly coupled to external threads of the threaded column 115. A lower portion 132 of the drive gear 125 is configured to couple to a top portion of the body 105 and held together with a retaining ring 140. The threaded column 115 is keyed to the body 105 in the opening 110 with axial translation mating features 120*a*, 120*b* configured to allow the threaded column 105 to translate column up and down 125 as the drive gear 130 rotates. Multiple up-stop tabs 145 are configured to prevent over expansion of the threaded column 100. Multiple springs 150 are used to regulate directional rotation of the drive gear 115, allowing rotation in a first direction and preventing rotation in a second direction. The multiple springs include a lower portion pressed into spring holes in the body 105. and an upper portion configured to engage a spring engagement feature on the drive gear 115. In use, the drive gear 130 is rotated 135 to translate the threaded column 115 up or down. The body 105 contains features for instrumentation to be attached and operated as well as graft windows for bone growth.

Both ends of the threaded column 130 include endplate mating splines 155 with a groove or slot 160. An endplate ring 165 is configured to be inserted in the groove or slot 160. The endplate ring 165 is made of a flexible material that can be radially compressed with a radial compression force, and then expand back to the original shape once the radial force is removed. The endplate ring 165 may be comprised of different materials, such as titanium or nitinol (NiTi).

Figure 2:
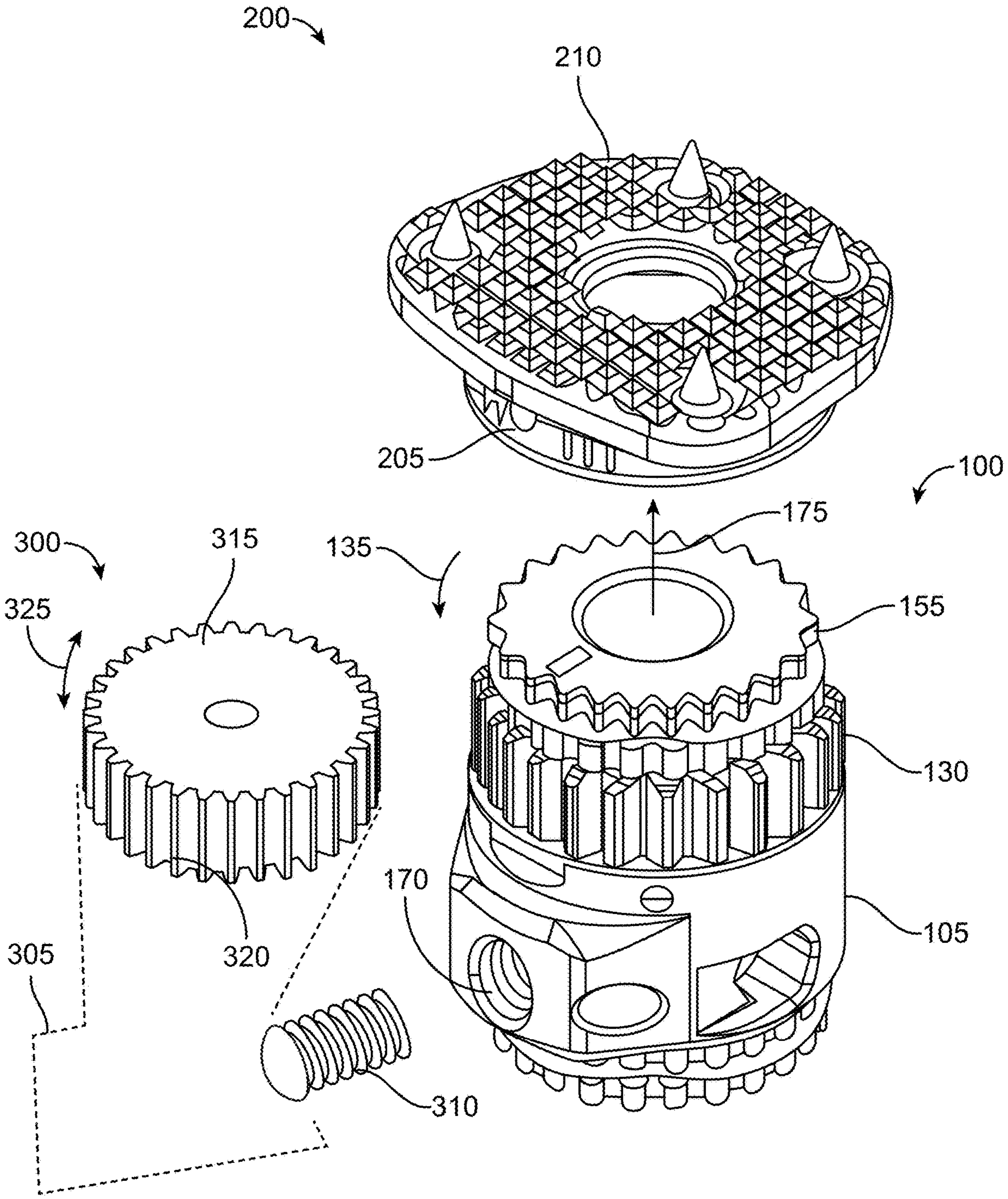
FIG. 2 is a perspective view showing the expandable column, an endplate, and an inserter to engage with the expandable column and to expand the expandable column.

FIG. 2 is a perspective view showing an endplate 200 approaching the expandable column 100. The endplate 200 includes a lower cylindrical wall 205 with an internal column mating spline surrounding a central opening sized to receive the endplate mating spline 155. The column mating spline 210 is configured to couple with the endplate mating spline 155 and endplate ring 165. The endplate 200 also includes an upper surface 210 configured to contact a vertebra. The upper surface 210 may vary in shape and/or geometry for the different spinal locations and/or anatomical needs.

An inserter 300 is configured to couple with the expandable column 100 and rotate the drive gear 130 and translate the threaded column for expansion. The inserter 300 includes a body 305 having a distal threaded portion 310 configured to couple with a threaded hole 170 in the body 105. The inserter 300 also includes an actuation gear 315 having teeth 320 configured to rotatably couple with the drive gear 130. The actuation gear 315 is configured to deliver a torque to the drive gear 130 to rotate the drive gear 130 and axially translate the threaded column 115 to expand 175 the expandable column 100.

Figure 3A:
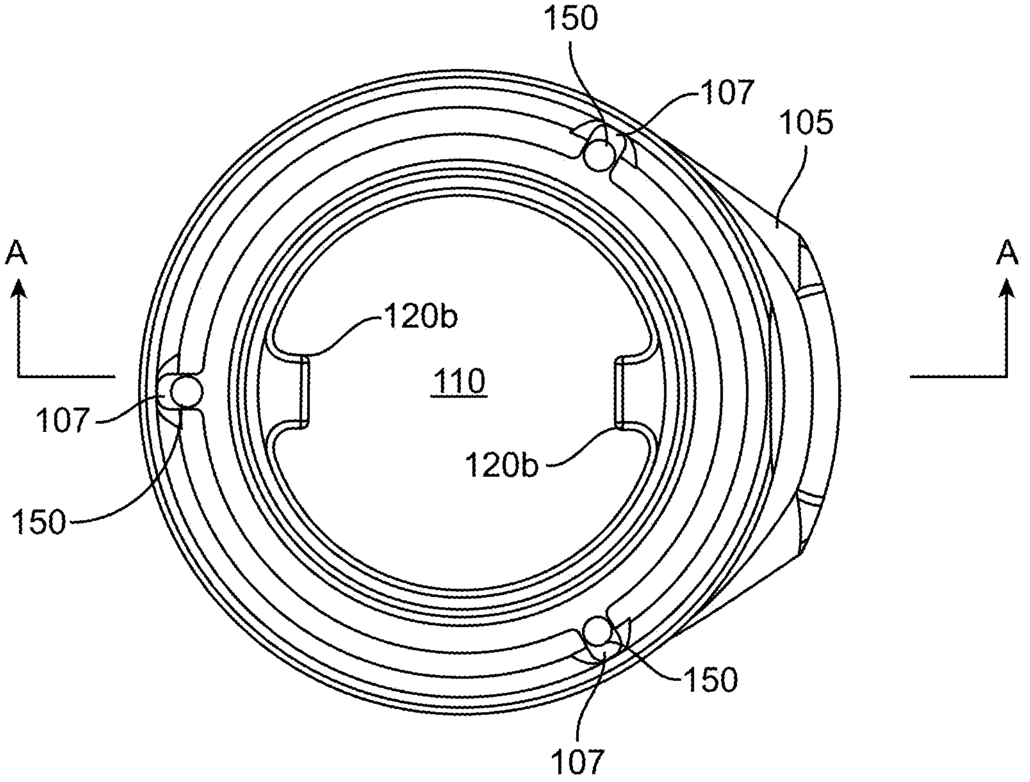
FIGS. 3A and 3B are a top view and sectional side view showing details of the springs coupled with the body.
Figure 3B:
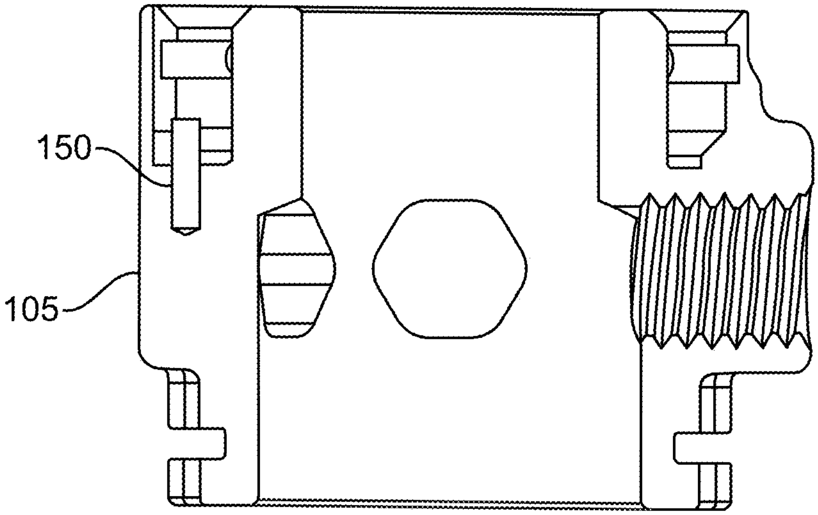

FIGS. 3A and 3B are a top view and sectional side view showing details of the springs 150 coupled with the body 105. The springs 150 are comprised of super-elastic nitinol (NiTi) with a lower portion pressed into pockets within the body 105 and an upper portion cantilevered upward. The springs 150 are configured such that they are cantilevered upward and engage a spring engagement feature, such as a drive gear track 180, on the lower portion of the drive gear 130. The drive gear track 180 is designed such that the torque 225 to overcome the cantilevered springs 150 is lesser when expanding the implant and greater when collapsing the implant, but configurations may exist where the torque is equal in both directions.

Figure 4A:
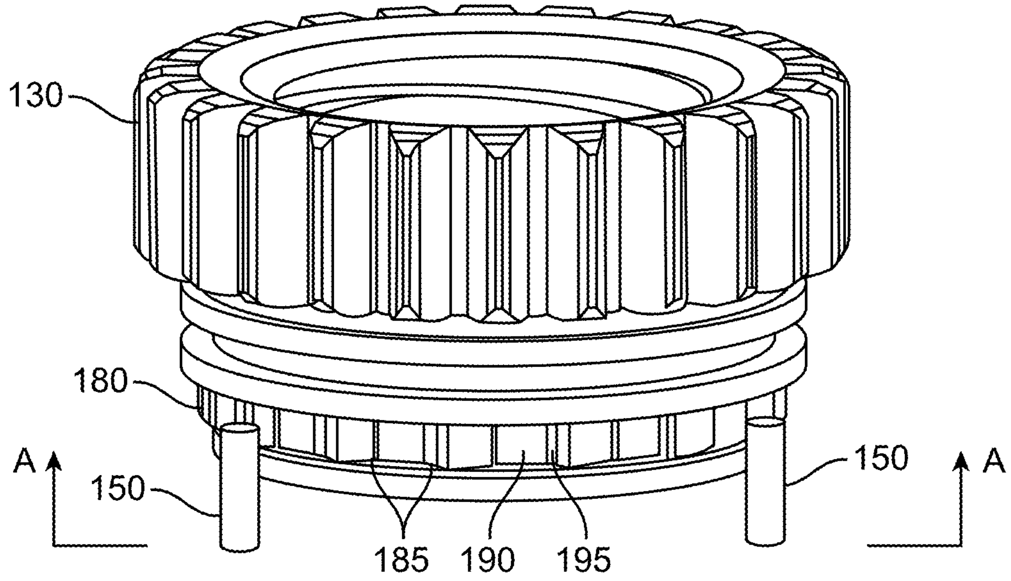
FIGS. 4A and 4B show a perspective view and a bottom view A-A of the spring engaging the drive gear track in a locked position, preventing rotation of the drive gear in a counterclockwise direction.
Figure 4B:
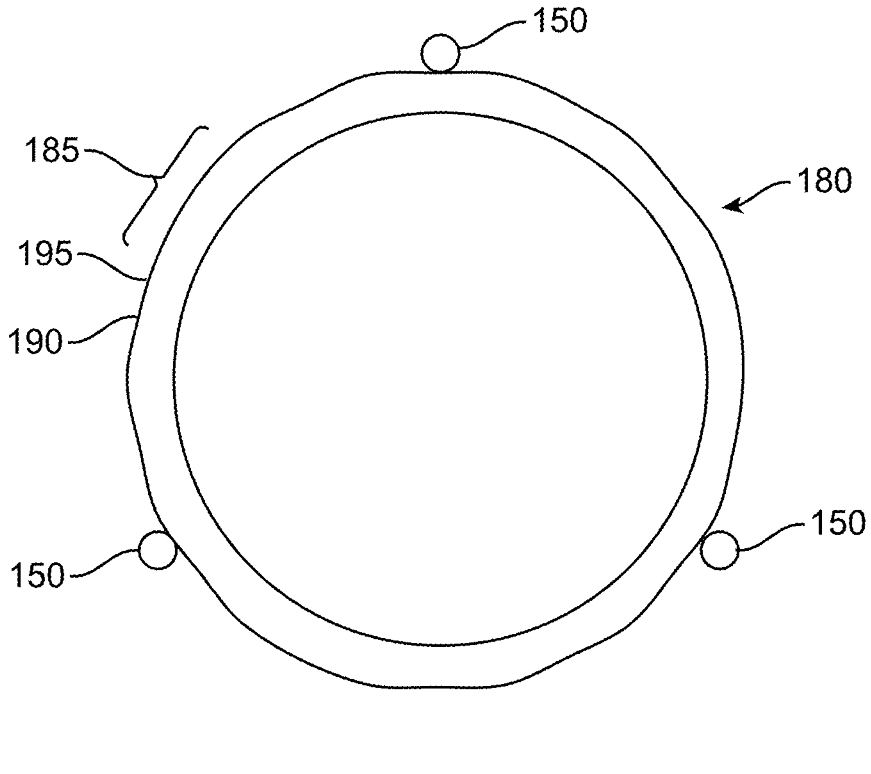

FIGS. 4A and 4B show a perspective view and a bottom view A-A of the spring 150 engaging the drive gear track 180 in a locked position, preventing rotation of the drive gear 130 in a counterclockwise direction. The drive gear track 180 includes a plurality of radial cut outs or pockets 185 having a gradual ramped wall 190 and steep angled wall 195. In the figures, the spring 150 is engaged with the steep angled wall 195 in the locked position, preventing rotation in the in the counterclockwise direction through friction.

Figure 5A:
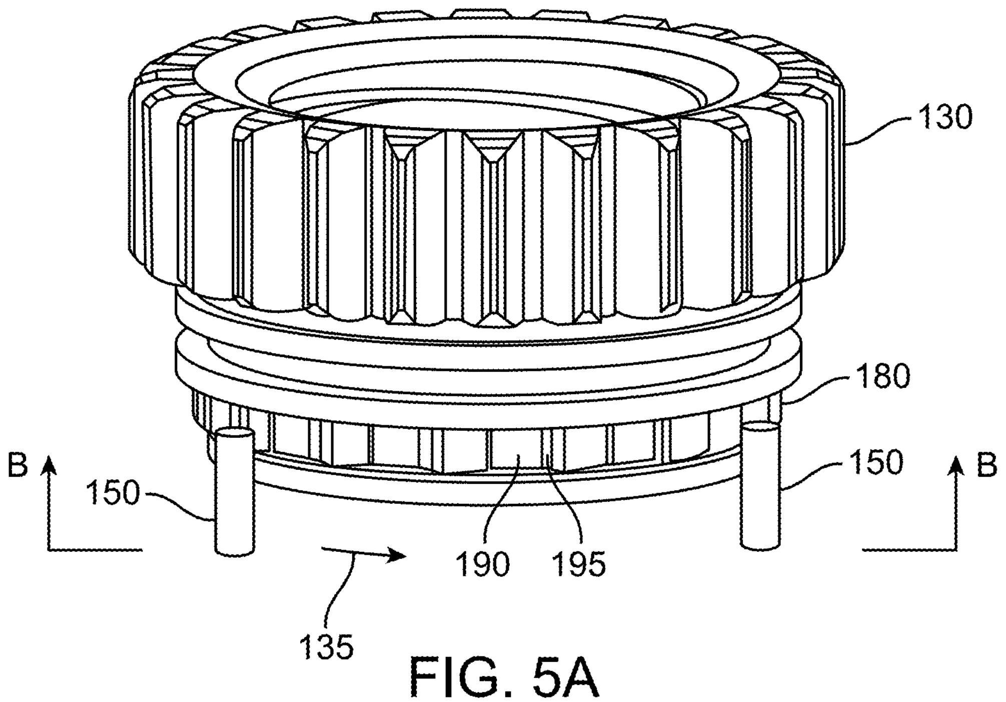
FIGS. 5A and 5B show a perspective view and a bottom view B-B of the spring engaging the drive gear track in an unlocked position, allowing rotation of the drive gear in a clockwise direction.
Figure 5B:
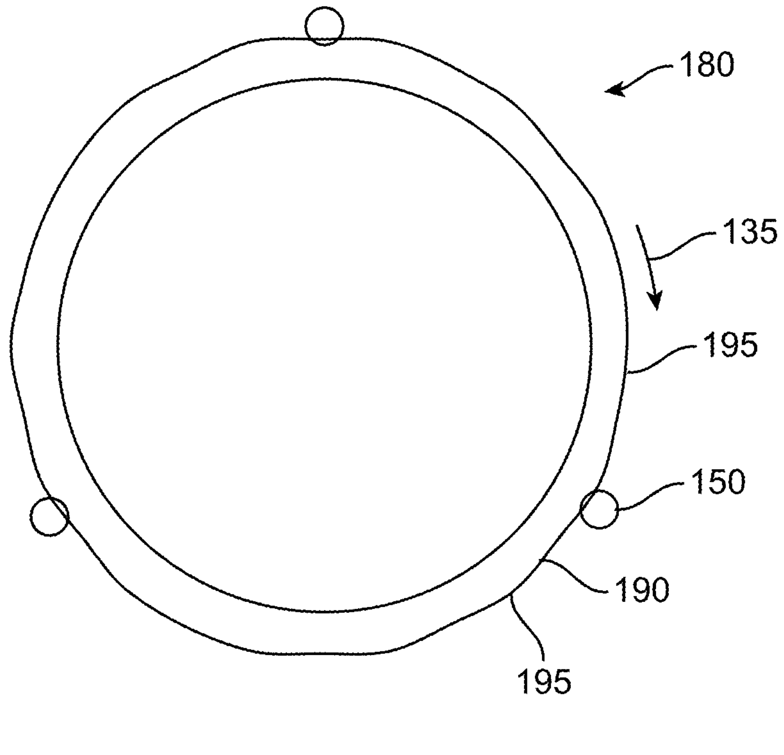

FIGS. 5A and 5B show a perspective view and a bottom view B-B of the spring 150 engaging the drive gear track 180 in an un-locked position, allowing rotation of the drive gear 130 in a clockwise direction. When the drive gear 130 is rotated in the clockwise direction 135, the cantilevered portion of the springs 150 contact the gradual ramped wall 190 and flex radially outward into relief pockets 107 in the body 105 until the adjacent pocket 185 is reached. When the next pocket 185 is reached. The springs compress radially inward into the pockets 185 through their cantilever spring force and prevent rotation of the drive gear 130 through friction.

Figure 6:
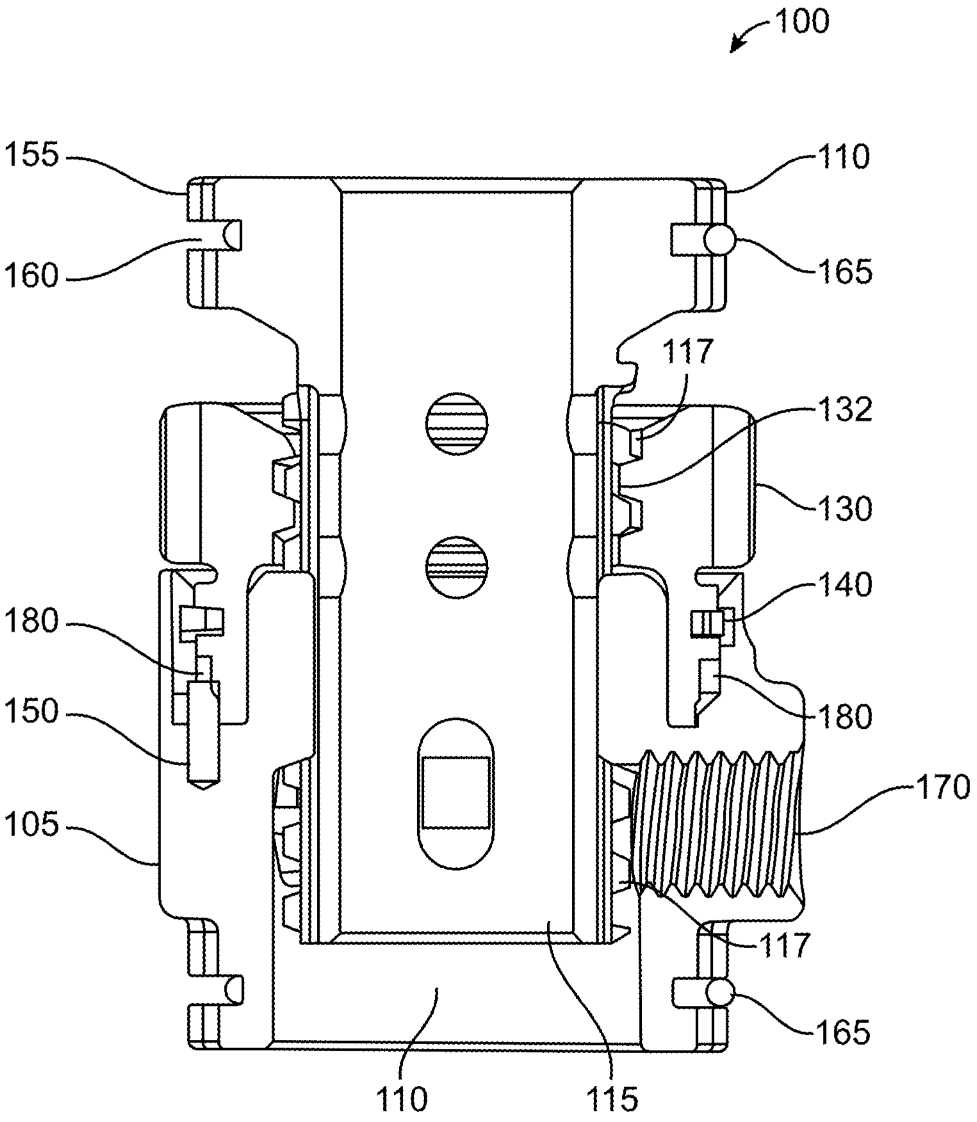
FIG. 6 is a sectional side view of the expandable column showing detail of the components.

FIG. 6 is a sectional side view of the expandable column 100. The body 105 includes the central opening 110 and the threaded column 115 is configured to sliding fit within the central opening 110. The drive gear 130 is threaded onto the threaded column 115. The drive gear 130 is coupled to the body 105 with the retaining ring 140 positioned in opposing slots in the drive gear 130 and body 105. The drive gear 130 includes internal threads 132 that engage the external threads 117 of the threaded column 115. that is Axial translation 125 of the threaded column 115 is done with a. The drive gear 125 includes internal threads 132 rotatingly coupled with external threads 117 on the threaded column 115. Multiple up-stop tabs 145 are configured to prevent over expansion of the threaded column 100. In use, the drive gear 130 is rotated 135 to translate the threaded column 115 up to expand.

Figure 7A:
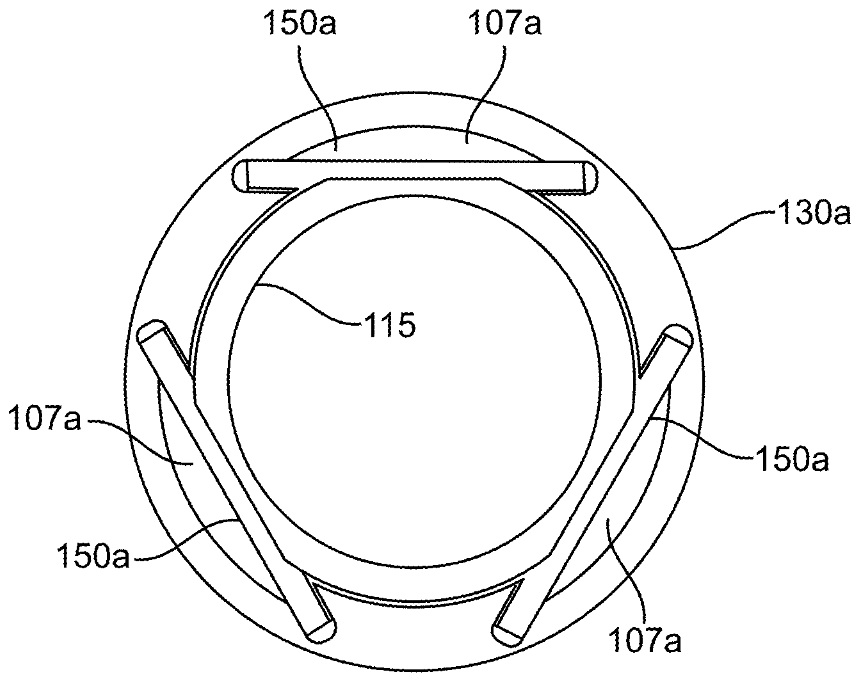
FIGS. 7A and 7B are top views showing alternate embodiment of an expandable column using non-cantilevered nitinol pins or springs.
Figure 7B:
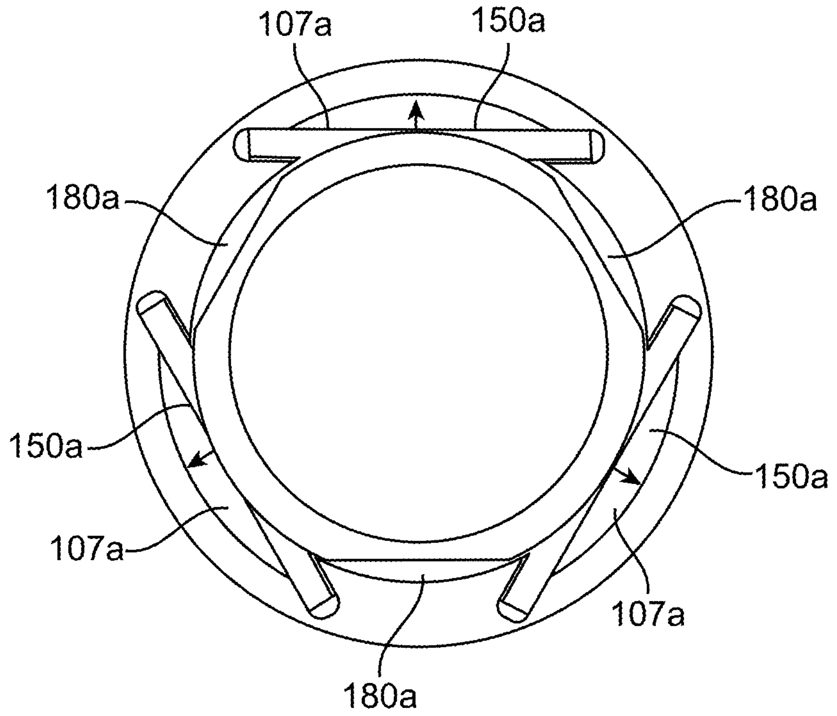

FIGS. 7A and 7B are top views showing an alternate embodiment of an expandable column 100 using a non-cantilevered nitinol pins or springs 150*a* mounted horizontally in the body 105*a* with a flexible center portion. The spring engagement feature is a drive gear track 180 with flat surfaces 180*a*. The springs 150*a* are coupled at each end to the body 105*a* with the central portion allowed to flex outward at the high point between the flat surfaces and then flex inward at the flat surface. In this embodiment, the drive gear 130*a* may be rotated on both the clockwise direction or counterclockwise direction.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable column with an auto-locking feature comprising:

a body having a central opening with a body axial translation feature;

multiple springs coupled to the body within the central opening;

a threaded column configured to slidingly fit into the central opening of the body, the threaded column having a column axial translation feature configured to engage the body axial translation feature to allow axial translation of the threaded column; and a drive gear threaded onto the threaded column and coupled to the body, the drive gear having a spring engagement feature configured to engage with the multiple springs;

wherein the spring engagement feature is a drive gear track with a plurality of radial cut outs or pockets having a gradual ramped wall and steep angled wall, and the multiple springs are cantilevered springs configure to engage the drive gear track during rotation;

wherein the multiple springs are used to regulate directional rotation of the drive gear, allowing rotation in a first direction and resisting rotation in a second direction to lock the threaded column.

2. The expandable column of claim 1, wherein the multiple springs are comprised of super-elastic material, such as nitinol.

3. The expandable column of claim 1, further comprising an endplate coupled to the threaded column.

4. The expandable column of claim 1, wherein rotation in the first direction expands the expandable column.

5. The expandable column of claim 1, wherein the torque to overcome the cantilevered springs contacting the gradual ramped wall is lesser during rotation in the first direction and contacting the steep angled wall greater during rotation in the second direction.

6. The expandable column of claim 1, further comprising an inserter configured to couple with the expandable column and configured to rotate the drive gear and translate the threaded column in the first direction for expansion.

7. The expandable column of claim 1, further comprising an inserter configured to couple with the expandable column and configured to rotate the drive gear and translate the threaded column in the first direction for expansion.

8. An expandable column with an auto-locking feature comprising:

a body having a central opening with a body axial translation feature;

multiple springs coupled to the body within the central opening;

a threaded column configured to slidingly fit into the central opening of the body, the threaded column having a column axial translation feature configured to engage the body axial translation feature to allow axial translation of the threaded column; and a drive gear threaded onto the threaded column and coupled to the body, the drive gear having a spring engagement feature configured to engage with the multiple springs;

wherein the spring engagement feature is a drive gear track with flat surfaces and the multiple springs are mounted horizontally in the body with a flexible center portion, the flexible central portion flexing outward at a high point between the flat surfaces and then flex inward at the flat surface;

wherein the multiple springs are used to regulate directional rotation of the drive gear, allowing rotation in a first direction and resisting rotation in a second direction to lock the threaded column.

9. The expandable column of claim 8, wherein the multiple springs are comprised of super-elastic material, such as nitinol.

10. The expandable column of claim 8, further comprising an endplate coupled to the threaded column.

11. The expandable column of claim 8, wherein rotation in the first direction expands the expandable column.

12. An expandable column with an auto-locking feature comprising:

a body having a central opening with a body axial translation feature;

multiple springs coupled to the body within the central opening;

a threaded column configured to slidingly fit into the central opening of the body, the threaded column having a column axial translation feature configured to engage the body axial translation feature to allow axial translation of the threaded column; and a drive gear threaded onto the threaded column and coupled to the body, the drive gear having a drive gear track configured to engage with the multiple springs;

wherein the drive gear track includes a plurality of radial cut outs or pockets having a gradual ramped wall and steep angled wall, and the multiple springs are cantilevered springs configured to engage the drive gear track during rotation.

13. The expandable column of claim 12, wherein the torque to overcome the cantilevered springs contacting the gradual ramped wall is lesser during rotation in the first direction and contacting the steep angled wall greater during rotation in the second direction.

14. The expandable column of claim 12, wherein the multiple springs are comprised of super-elastic material, such as nitinol.

15. The expandable column of claim 12, further comprising an endplate coupled to the threaded column.

16. The expandable column of claim 12, further comprising an inserter configured to couple with the expandable column and configured to rotate the drive gear and translate the threaded column in the first direction for expansion.

17. An expandable column with an auto-locking feature comprising:

a body having a central opening;

multiple springs having a lower portion pressed into spring holes in the body with a cantilevered upper portion;

a threaded column axially coupled to the body; and a drive gear having a drive gear track rotatingly coupled to the body and the threaded column, the drive gear being configured to rotate and translate the threaded column axially up or down, the drive gear track having a plurality of radial cut outs or pockets with a gradual ramped wall and steep angled wall;

wherein the cantilevered upper portion of the springs are configured to engage the drive gear track, wherein rotation in a first direction translates the cantilevered upper portion along the gradual ramped wall, and rotation in a second direction translate s the cantilevered upper portion into the steep angled wall locking the cantilevered upper portion and preventing further rotation.

18. The expandable column of claim 17, wherein the torque to overcome the cantilevered spring contacting the gradual ramped wall is lesser during rotation in the first direction and contacting the steep angled wall greater during rotation in the second direction.

19. The expandable column of claim 17, wherein the multiple springs are comprised of super-elastic material, such as nitinol.

20. The expandable column of claim 17, further comprising an endplate coupled to the threaded column.

21. The expandable column of claim 17, further comprising an inserter configured to couple with the expandable column and configured to rotate the drive gear and translate the threaded column in the first direction for expansion.

* * * * *